United States Patent
Hart

Patent Number: 5,876,365
Date of Patent: Mar. 2, 1999

[54] BANDAGE ASSEMBLY

[76] Inventor: Robert L. Hart, 1525 Olive St., Indianapolis, Ind. 46203

[21] Appl. No.: 905,199

[22] Filed: Aug. 1, 1997

Related U.S. Application Data

[60] Provisional application No. 60/031,019 Nov. 18, 1996.

[51] Int. Cl.$^6$ ........................................................ A61F 13/00
[52] U.S. Cl. ........................................................ 602/79
[58] Field of Search ........................... 602/41–59, 79; 128/888, 889

[56] References Cited

U.S. PATENT DOCUMENTS

| | | | |
|---|---|---|---|
| 3,307,547 | 3/1967 | Jones et al. | 602/79 |
| 4,399,816 | 8/1983 | Spangler | 602/57 |
| 4,641,643 | 2/1987 | Greer | 602/42 X |
| 4,732,146 | 3/1988 | Fasline et al. | 602/79 |
| 5,086,763 | 2/1992 | Hathman | 602/79 X |
| 5,167,613 | 12/1992 | Karami et al. | 602/57 |
| 5,449,340 | 9/1995 | Tollini | 602/57 X |
| 5,456,660 | 10/1995 | Reich et al. | 602/79 |
| 5,662,599 | 9/1997 | Reich et al. | 602/79 |
| 5,702,356 | 12/1997 | Hathman | 602/79 X |

FOREIGN PATENT DOCUMENTS 9424972  11/1994  WIPO.

*Primary Examiner*—Richard J. Apley
*Assistant Examiner*—Kim M. Lee
*Attorney, Agent, or Firm*—Woodard, Emhardt, Naughton Moriarty & McNett

[57] ABSTRACT

One embodiment is an adhesive bandage with an opening in the middle in which the wound is exposed after the bandage is applied to the skin. A removable cap is fastened on the bandage with hook-and-loop material to cover the opening and thereby protect the wound. Another embodiment has a base panel with a transverse strip of hook-and-loop fastener material at one edge, and strips of hook-and-loop fastener material extending from the other end to wrap around a wounded body part and connect to the transverse strip and forms an opening which frames the wound. A removable cap is fastened over the opening with hook-and-loop-fastener material fastened to the extending strips.

3 Claims, 2 Drawing Sheets

BANDAGE ASSEMBLY

BACKGROUND OF THE INVENTION

This invention relates generally to adhesive bandages and, more particularly, to a bandage assembly enabling access to a wound without tearing off the adhesive part from a patient's skin.

DESCRIPTION OF THE PRIOR ART

The prior art known to me prior to filing this application was adhesive bandages covering a wound, or some kind gauze or other protective material taped in place by adhesive tape. Either way, a caregiver could not have access to the wound without tearing the tape away from the patient's skin, with the attendant discomfort or pain. The object of this invention is to avoid that problem.

SUMMARY OF THE INVENTION

Described briefly, according to a typical embodiment of this invention, an adhesive bandage has an opening in the middle in which the wound is exposed after the bandage is applied to the skin. An easily attachable, but readily separable when intended, fastening system is provided adjacent the opening to receive mating materials on a cover piece which can be readily placed on the bandage to cover the opening and thereby protect the wound. The cover piece can be easily removed when desired to view and attend to the wound, without pulling the adhesive bandage off of the skin. The cover piece can be discarded and replaced by a new one, if desired, without disturbing the bandage attachment to the patient's skin.

In another embodiment, the bandage is made in different proportions for application to a body part in a wrap-around manner with a couple of hook-and-loop fastener strips situated to cooperate with a base panel to frame the wound when the panel is wrapped around, and a transverse strip attached to the parallel strips. A cover with hook-and-loop fastener strips thereon mateable with those on the bandage covers the opening and is removable for access to the wound without removing the bandage from the skin.

DESCRIPTION OF THE PREFERRED EMBODIMENTS

Figures 1, 2:
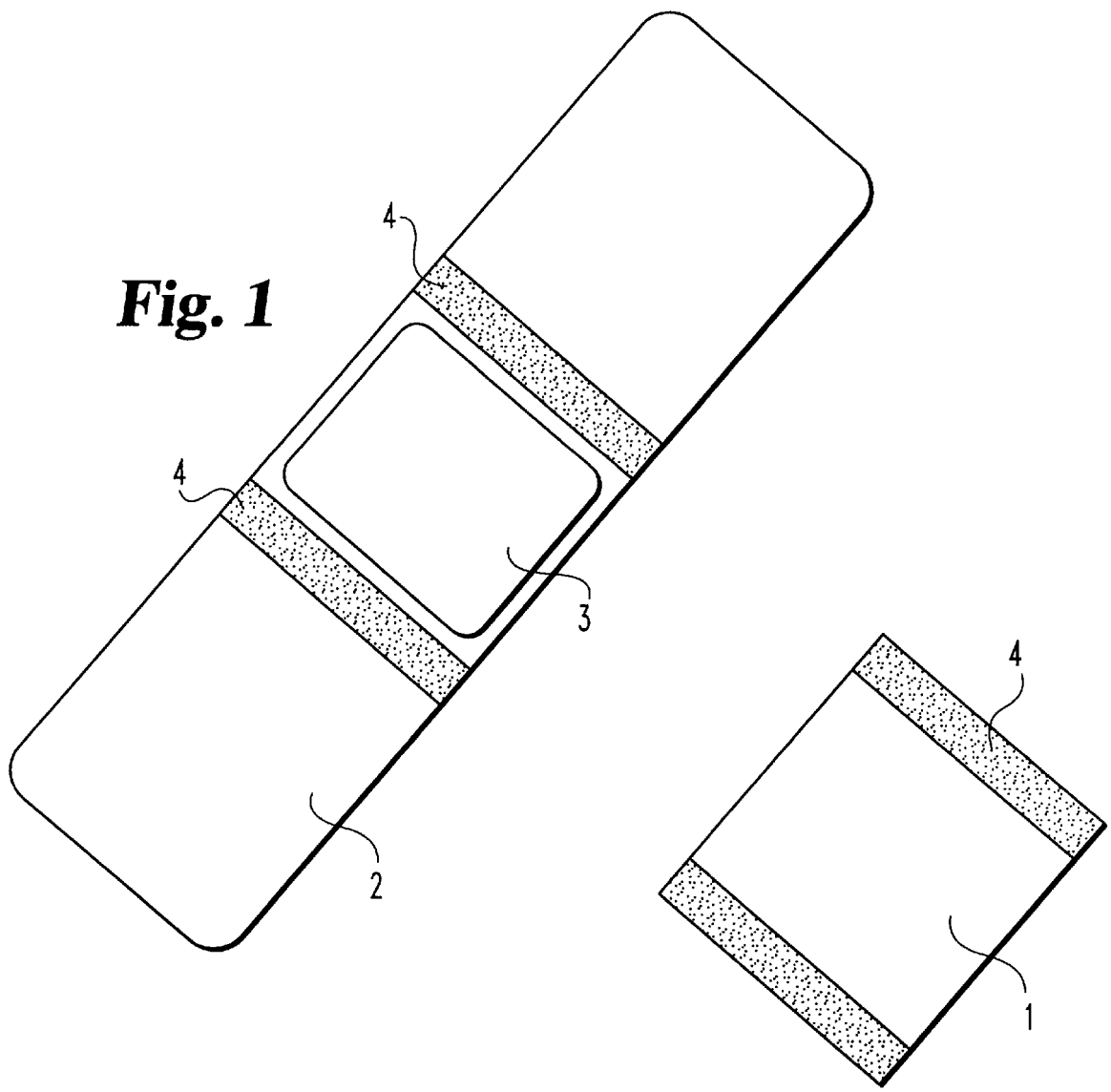
FIG. 1 is a top view of the bandage.
FIG. 2 is a bottom view of the cap.
Figure 3:
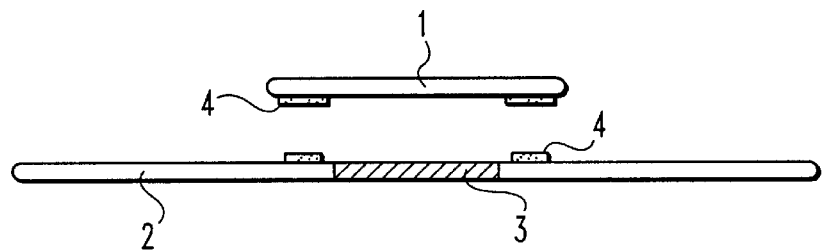
FIG. 3 is an exploded sectional view of the bandage assembly with the cap over the top of bandage.

The cap 1, of FIG. 2 with the hook and loop material strips 4, mounts on bandage 2, FIG. 1, which has an opening 3 for the cap to cover when placed over the opening 3, FIG. 3 the bandage 2 and the strips 4 of the cap are pressed together with the strips 4 of the bandage.

Figure 4:
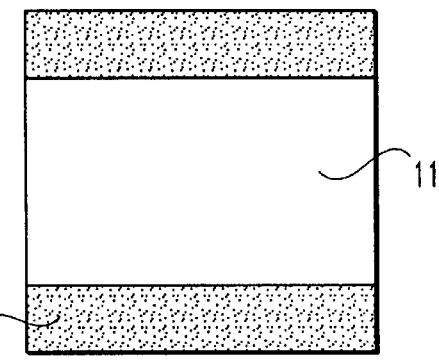
FIG. 4 is a bottom view of the cap for the FIG. 5 bandage.
Figure 5:
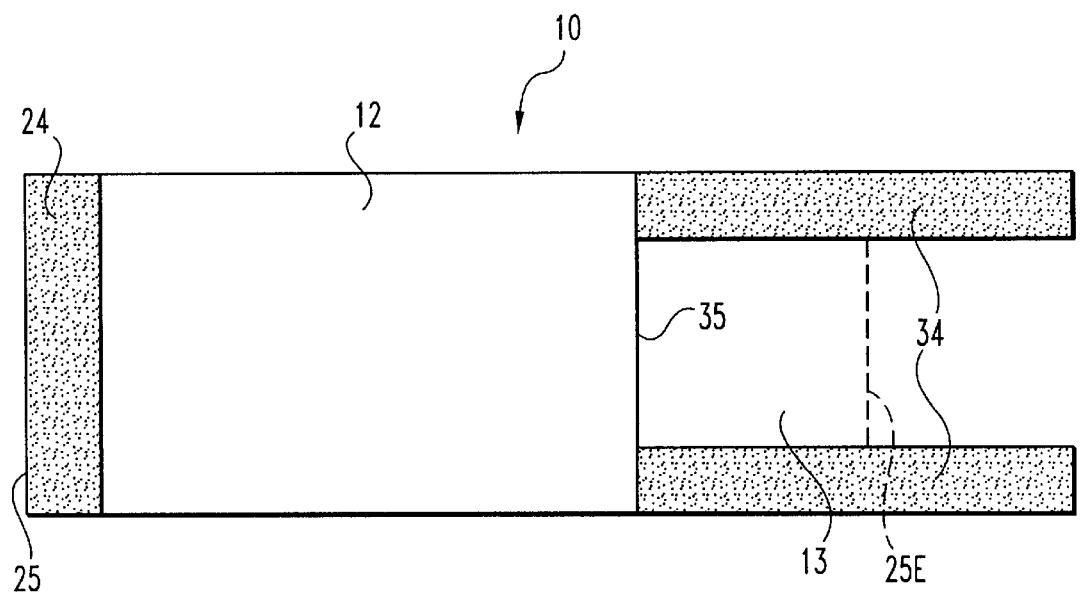
FIG. 5 is a top view of a wrap-around bandage embodiment of the invention.

In the embodiment of FIGS. 4 and 5, the bandage 10 has a base 12 with a transverse strip 24 of hook-and-loop material fixed to one end and a pair of parallel strips 34 of hook-and-loop material fixed to the opposite end. The length of the base and strips 34 is sufficient to wrap around a body part, with the strips 34 and edge 35 of the base 12 bracketing the skin wound. The transverse strip 24 is pressed onto the strips 34 so edge 25 is at dotted line 25E, thus framing the wound and providing access to it through opening 13. Then cap 11, FIG. 4 will fit over the opening 13 of the wrap-around bandage 10. FIG. 5 with its strips 14 pressed on strips 34 to cover the wound that is otherwise exposed in the opening. The use of the hook-and-loop material on strips 14, 24 and 34, makes the bandage assembly well adapted for adjustments.

In either embodiment, the cap and bandage can be of multiple shapes and sizes. The cap can be plastic, cloth, gauze-like and coupled with the advantage of elastic, adhesive, wrap-around and other like fabrics. The bandage of FIGS. 1 and 3 can be applied to the skin in a conventional way as with typical adhesive bandages. The placement can be precise. With the cap removed, the wound can be readily seen through the opening to aid in the positioning of the bandage upon the skin. Then it can be closed by applying the cap to cover the wound. The cap can be removed subsequently, whenever desired, without discomfort to the patient, because it is only necessary to pull it off hook-and-loop fasteners, without peeling the adhesive bandage from the patient's skin. A physician or other caregiver can quickly view the wound and add medication and/or treat the patient, as desired. The cap can be discarded and replaced with a fresh one, or can be re-installed readily if still in good condition.

In the wrap-around embodiment, an overall length of the base and parallel strips can be chosen to most appropriately fit the place on a finger, arm, leg, neck, or the head of the patient so that when wrapped around the relevant body part, there will be sufficient length of the parallel strips to enable wrapping the base around the body part and pressing the transverse strip 24 against the strips 34 at a location such as to both securely wrap the bandage around the body part, and position the opening 13 so that it properly frames the wound. Then the cap 11 can be installed by pressing the strips 14 thereof on strips 34 of the bandage. In this embodiment, adhesive to attach to the skin can be used on the back of base 12, if desired, but is not necessary.

I claim:

1. A bandage assembly comprising:

a base with a bottom adapted to attach to the skin of a patient and which provides an opening to surround a feature on the skin;

reusable fastening material on the top of the base;

two parallel strips of reusable fastening material having proximal ends spaced apart at an edge of the base on opposite sides of the opening; and a cap big enough to cover the opening and which has reusable fastening material on it cooperable with the fastening material on top of the base so the cap can be put on the base and fastened there to cover the opening and protect the skin feature, but can be removed without tools and then can be put back on the base again using the same cooperating fastening materials to retain the cap to cover the opening and protect the feature;

the bandage assembly being adapted to wrap around a body part, with the fastening material on parallel strips fastened on the base that extend from one edge of the base and the fastening material is also fastened to the base at the other edge of the base;

wherein the base and parallel strips are long enough for the parallel strips to be wrapped around the body part and pressed onto the fastening material at the other edge of the base at different locations on the parallel strips to adjust the size of the assembly; and wherein the two edges of the base, and eges of the parallel strips form the opening to surround the skin feature.

2. The bandage assembly of claim 1 wherein the fastening material at the other edge of the base is on a strip across the other edge, and the locations of attachment of the parallel strips to the strip across effect the size of the opening.

3. The bandage assembly of claim 2 and wherein the fastening material on the parallel strips connects to the fastening material on the strip across.

* * * * *